United States Patent
Baxi et al.

(10) Patent No.: US 10,022,073 B2
(45) Date of Patent: Jul. 17, 2018

(54) WEARABLE APPARATUS WITH A STRETCH SENSOR

(71) Applicant: Intel Corporation, Santa Clara, CA (US)

(72) Inventors: Amit S. Baxi, Thane (IN); Vincent S. Mageshkumar, Navi Mumbia (IN)

(73) Assignee: Intel Corproation, Santa Clara, CA (US)

( * ) Notice: Subject to any disclaimer, the term of this patent is extended or adjusted under 35 U.S.C. 154(b) by 163 days.

(21) Appl. No.: 14/664,095

(22) Filed: Mar. 20, 2015

(65) Prior Publication Data
US 2016/0270700 A1    Sep. 22, 2016

(51) Int. Cl.
*G01L 1/00* (2006.01)
*G01L 5/00* (2006.01)
(Continued)

(52) U.S. Cl.
CPC .......... *A61B 5/1121* (2013.01); *A61B 5/6802* (2013.01); *A61B 5/6828* (2013.01); *A61B 5/6831* (2013.01); *A61B 5/01* (2013.01); *A61B 5/0488* (2013.01); *A61B 5/1118* (2013.01); *A61B 5/14517* (2013.01); *A61B 5/7225* (2013.01); *A61B 2562/0261* (2013.01); *A61B 2562/164* (2013.01); *A61B 2562/166* (2013.01)

(58) Field of Classification Search
CPC ........ A61B 5/11; A61B 5/1121; A61B 5/1118
USPC ............. 73/768, 774, 776, 862.381, 862.392
See application file for complete search history.

(56) References Cited

U.S. PATENT DOCUMENTS 4,715,235 A * 12/1987 Fukui et al. ............. G01D 5/16
338/114
5,442,729 A * 8/1995 Kramer et al. ...... A61B 5/6806
128/925
(Continued)

FOREIGN PATENT DOCUMENTS

EP         2783630 A1    10/2014
WO     2006034201 A3     3/2006
(Continued)

OTHER PUBLICATIONS

Authors: Aaron P. Gerratt , Hadrien O. Michaud , and Stéphanie P. Lacour, Title: Elastomeric Electronic Skin for Prosthetic Tactile Sensation, Date: Mar. 4, 2015, Publisher: Adv. Functional. Materials, vol. 25, pp. 2287-2295.*

(Continued)

*Primary Examiner* — Lisa Caputo
*Assistant Examiner* — Roger Hernandez-Prewit
(74) *Attorney, Agent, or Firm* — Schwabe, Williamson & Wyatt, P.C.

(57) ABSTRACT

Embodiments of the present disclosure provide techniques and configurations for a wearable sensor apparatus. In one instance, the apparatus may comprise a flexible substrate and conductive fabric component that comprises a first length and that may be attachably mounted on the flexible substrate. The conductive fabric component, in response to a direct or indirect application of external force to the flexible substrate, may stretch between the first length and a second length that is greater than the first length, and generate an electric parameter based at least in part on an amount of the applied external force. Other embodiments may be described and/or claimed.

24 Claims, 9 Drawing Sheets

(51) Int. Cl.
*A61B 5/11* (2006.01)
*A61B 5/00* (2006.01)
A61B 5/0488 (2006.01)
A61B 5/01 (2006.01)
A61B 5/145 (2006.01)

(56) References Cited

U.S. PATENT DOCUMENTS

| | | |
|---|---|---|
| 5,847,639 A | 12/1998 | Yaniger |
| 2009/0143704 A1* | 6/2009 | Bonneau et al. .... A61B 5/1038 600/595 |
| 2010/0049450 A1* | 2/2010 | Nagakubo et al. ..... G01L 5/228 702/41 |
| 2010/0274447 A1* | 10/2010 | Stumpf .................... G01D 1/00 701/36 |
| 2012/0118066 A1 | 5/2012 | Majidi et al. |

FOREIGN PATENT DOCUMENTS

| | | |
|---|---|---|
| WO | 2006034291 A2 | 3/2006 |
| WO | 2014204323 A1 | 12/2014 |

OTHER PUBLICATIONS

International Search Report and Written Opinion dated May 11, 2016, issued in corresponding International Application No. PCT/US2016/017415, 14 pages.
Office Action in Primary Examination dated Dec. 5, 2016, issued in corresponding Taiwan Patent Application No. 105104631, 23 pages.
2nd Office Action and Search Report dated Jul. 31, 2017, issued in corresponding Taiwan Patent Application No. 105104631, 27 pages.
International Preliminary Report on Patentability dated Oct. 5, 2017, issued in related International Application No. PCT/US2016/017415, 11 pages.
Baxi, et al., "Wearable Sensor Apparatus with Multiple Flexible Substrates," U.S. Appl. No. 14/563,801, filed Dec. 8, 2014, 40 pages.
MVN BioMech, 3D Human Kinematics, Xsens [online] [retrieved on Nov. 23, 2016], Retrieved from the Internet: <URL: www.xsens.com/products/mvn-biomech/>.
Third Office Action and Search Report dated Feb. 1, 2018, issued in corresponding Taiwan Patent Application No. 105104631, 28 pages.

* cited by examiner

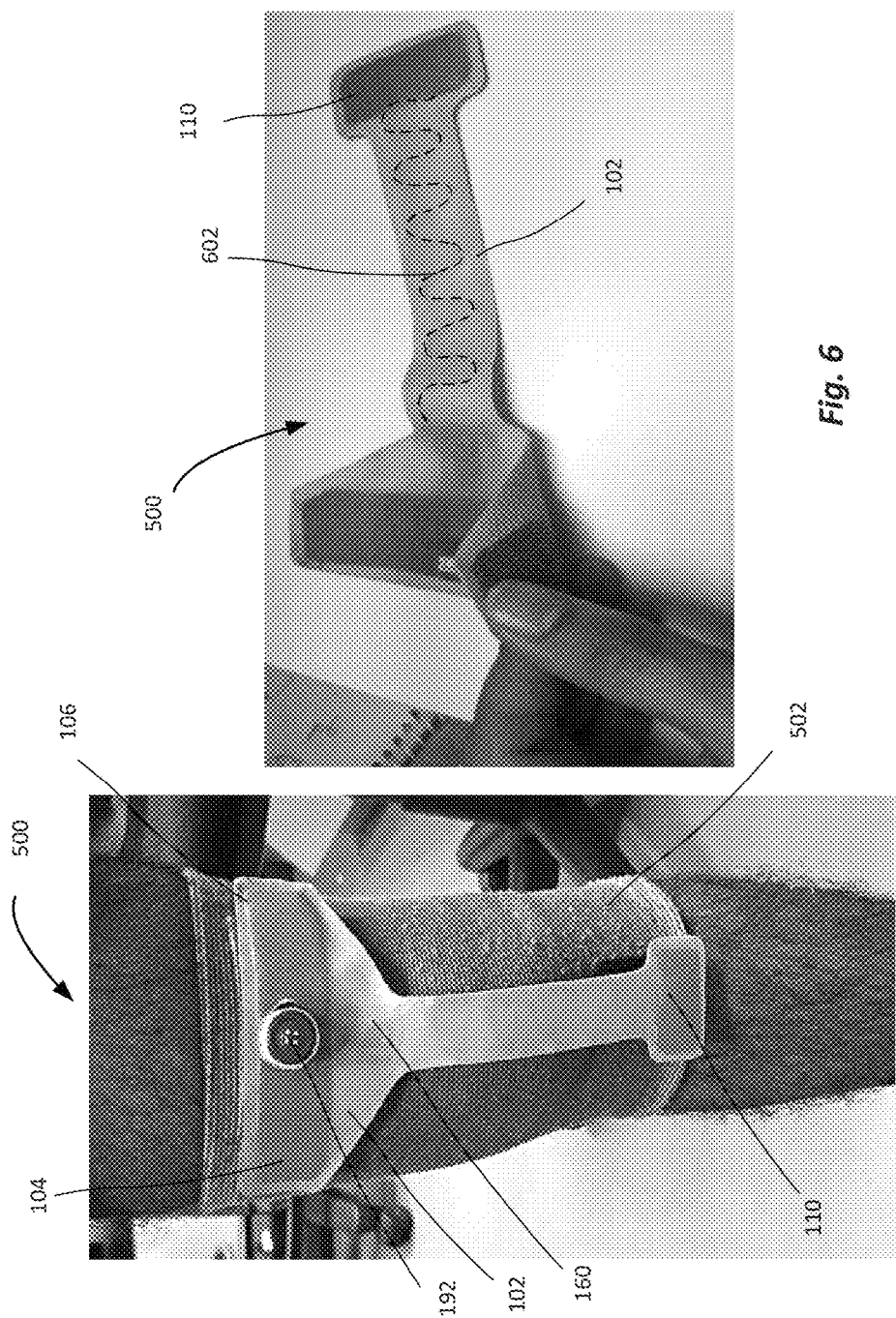

WEARABLE APPARATUS WITH A STRETCH SENSOR

FIELD

Embodiments of the present disclosure generally relate to the field of sensor devices, and more particularly, to wearable sensing systems with stretch sensors that may be conformal with a human body.

BACKGROUND

With advancements in various technologies, wearable sensing devices or systems are increasingly popular. A wearable sensing system may need to be comfortably attached to the human body, and may be able to measure and quantify stretch, strain, or bending of a human body and/or different parts of the body, such as joints, wrists, fingers, ankles, knees, and the like. However, the existing sensors to monitor stretch, strain, bending, and the like may have limited ability to effectively sense around movable spots of the human body. Furthermore, the existing sensors may be expensive, may have limited ability to integrate into wearable devices, may be fragile or susceptible to breaks, or may provide limited accuracy.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

FIGS. 5-8 illustrate different views of an example wearable sensor apparatus 100 comprising a conformal motion sensing system, in accordance with some embodiments.

DETAILED DESCRIPTION

Embodiments of the present disclosure include techniques and configurations for a wearable sensor apparatus. In accordance with embodiments, the apparatus may comprise a flexible substrate and conductive fabric component that comprises a first length and that may be attachably mounted on the flexible substrate. The conductive fabric component, in response to a direct or indirect application of external force to the flexible substrate, may stretch between the first length and a second length that is greater than the first length, and generate an electric parameter based at least in part on an amount of the applied external force.

In the following detailed description, reference is made to the accompanying drawings that form a part hereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), (A) or (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

Figure 1:
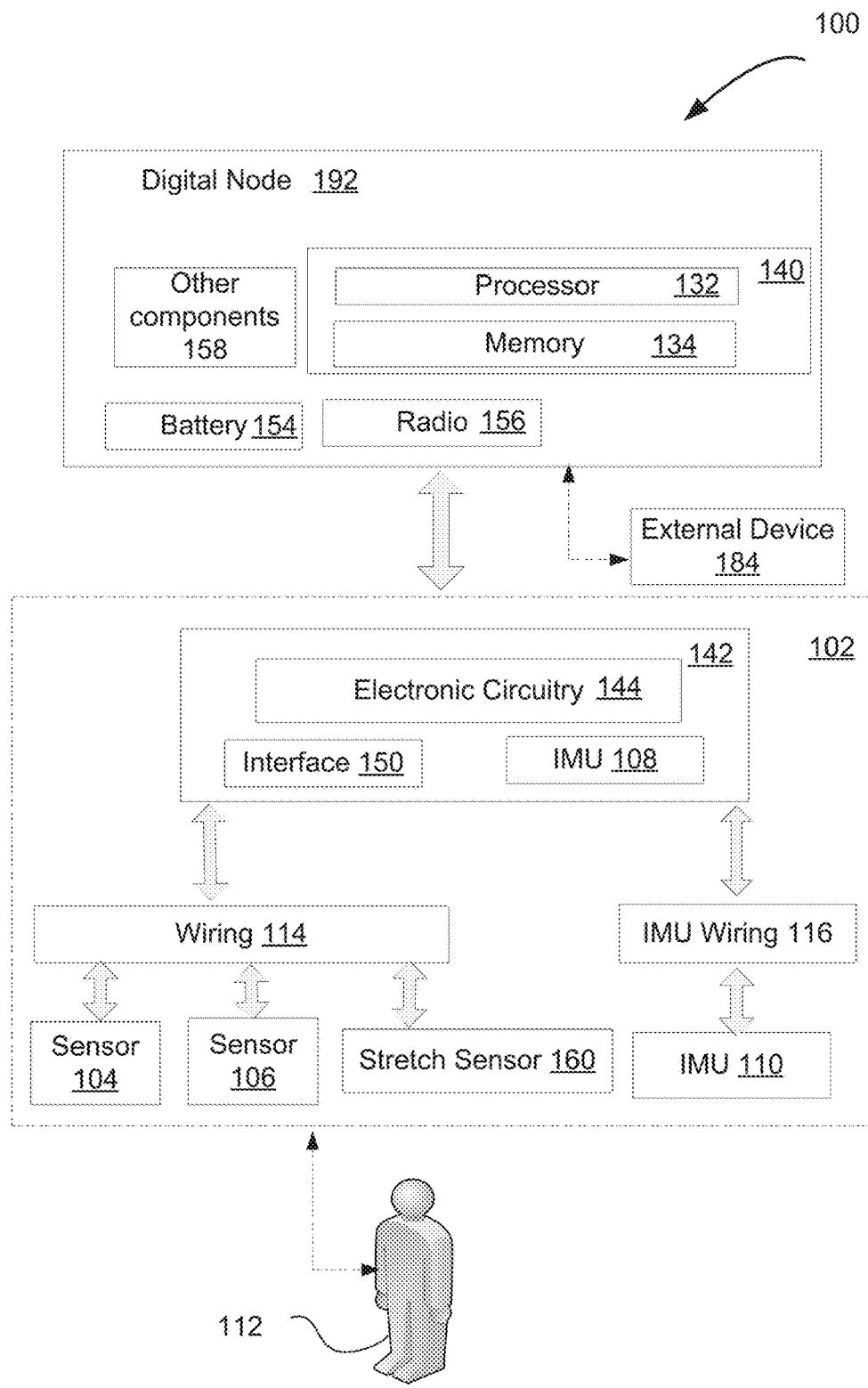
FIG. 1 is a block diagram illustrating an example wearable sensor apparatus incorporated with the teachings of the present disclosure, in accordance with some embodiments.

FIG. 1 is a block diagram illustrating an example wearable sensor apparatus 100 incorporated with the teachings of the present disclosure, in accordance with some embodiments. The apparatus 100 may comprise a conformal body 102 (comprising, e.g., a flexible substrate indicated by a dashed line) configured to be attachable to a user's body 112 in order to conduct measurements associated with the functioning of the user's body 112 and user's activities. In embodiments, the conformal body 102 may take different shapes and/or sizes, such as a strap, a band, or the like, in order to conform to different parts of the user's body 112. The conformal body 102 may be made of elastic fabric, elastomer, polymer, or other suitable materials.

The apparatus 100 may include a stretch sensor 160 disposed on the conformal body 102 and configured to provide measurements of an electric parameter generated by the stretch sensor 160 in response to stretching that may be caused by an external force. In some embodiments, the stretch sensor 160 may comprise a conductive fabric based sensor, configured to provide readings of resistance parameter that the sensor 160 may generate in response to an application of external force, such as bending of a knee or an arm, for example. The embodiments of the stretch sensor 160 will be described in reference to FIGS. 2-4.

The apparatus 100 may further include a plurality of sensors 104, 106 that may be disposed around conformal body 102 to be in contact with a user's body 112. For example, the sensors 104, 106 may be placed around an inner or outer side of the flexible substrate comprising the conformal body 102, to enable measurements associated with the user's body 112. In some embodiments, the sensors 104, 106 may be built in (e.g., embedded in, glued to, and the like) the flexible substrate of the conformal body 102. The sensors 104, 106 may provide readings related to various user body functions. For example, the sensors 104, 106 may include, but may not be limited to, electromyography (EMG) sensors, temperature sensors, sweat chemical sensors, motion sensors, optical photodiodes, electrocardiogram (ECG) electrodes, galvanic skin response (GSR) sensors, piezo crystals, pressure sensors, or the like.

It should be noted that sensors 104, 106, 160 are shown in FIG. 1 for illustration only and are not limiting the implementation of apparatus 100. It will be appreciated that any number or types of sensors may be used in the apparatus 100.

The apparatus 100 may further include one or more inertial measurement units (IMU) 108 and 110 disposed around the conformal body 102 and configured to provide motion-related measurements associated with the user's body 112. The disposition of the IMU 108 and 110 around the conformal body 102 will be discussed in detail in reference to FIGS. 5-8.

The apparatus 100 may further include a sensor front end module 142 that may be electrically connectable with the sensors 104, 106, and 160. The sensor front end module 142 may comprise a printed circuit board (PCB) and may be disposed on the flexible substrate comprising the conformal body 102. In embodiments, the sensor front end module 142 may be disposed on an outer side of the flexible substrate comprising the conformal body 102.

The sensor front end module 142 may include electronic circuitry 144 configured to receive and process readings provided by the sensors 104, 106, and 160. The circuitry 144 may be further configured to provide power and excitation to the sensors 104, 106 (if required), transduce the sensor signals into voltage, amplify and condition the sensor signals. An example application of the electronic circuitry 144 to read and process the signals from the stretch sensor 160 will be described in reference to FIG. 3.

The front end module 142 (e.g., circuitry 144) may be electrically coupled with the sensors 104, 106, and 160 via wiring 114. Wiring 114 may comprise wires to electrically connect respective sensors with the sensor front end module 142.

Some of the IMU of the apparatus 100 (e.g., IMU 108) may be integrated in the PCB providing the sensor front end module 142 or digital node 192 (described below). Some of the IMU (e.g., IMU 110) may be disposed in other parts of the conformal body 102, e.g., at a distance from the sensor front end module 142. As shown, IMU 110 may be electrically coupled with the sensor front end module 142 via IMU wiring 116. IMU wiring 116 may be configured as multiple wired connections comprising a multi-wire bus to carry a power signal, ground, and data signals provided by to the IMU 110. Wiring 114 and IMU wiring 116 may be built in (e.g., embedded, embroidered, woven, imprinted, and the like) the flexible substrate of the conformal body 102.

The apparatus 100 may further include a digital node 192 that may be mechanically and electrically coupled with the sensor front end module 142. For example, the sensor front end module 142 may include an interface 150 (e.g., electric connector such as multi-pin contact) to provide mechanical and electric coupling with the digital node 192. The digital node 192 may be configured to further process the readings provided by the sensors 104, 106, 160 and IMU 108 and 110.

In some embodiments, the digital node 192 may include a processing unit 140 having a processor 132 configured to process the readings (signals) provided by the sensors 104, 106, 160. The processing unit 140 may include memory 134 having instructions that, when executed on the processor 132, may cause the processor 132 to perform signal processing. The digital node 192 may include a battery 154 configured to provide power supply to the digital node 192 and, more generally, to the components of the apparatus 100. The digital node 192 may include a radio 156 to transmit processed data resulting from processing the sensor readings for further processing, e.g., to an external device 184 (e.g., mobile or stationary computing device). The digital node 192 may include a mating connector (not shown) to mate the interface 150 of the sensor front end module 142.

The digital node 192 may include other components 158 necessary for the functioning of the apparatus 100. For example, other components 158 may include communications interface(s) to enable the apparatus 100 to communicate over one or more wired or wireless network(s) and/or with any other suitable device, such as external device 184.

In summary, the digital node 192 may be configured to supply power to sensor front end module 142, sensors 104, 106, 160, and IMU 108, 110, and perform data acquisition, processing, and transmission. The digital node 192 may be further configured to perform signal de-noising, feature extraction, classification, data compression, and wireless transmission of sensed signals over a network (e.g., local wireless network, not shown).

Figure 2:
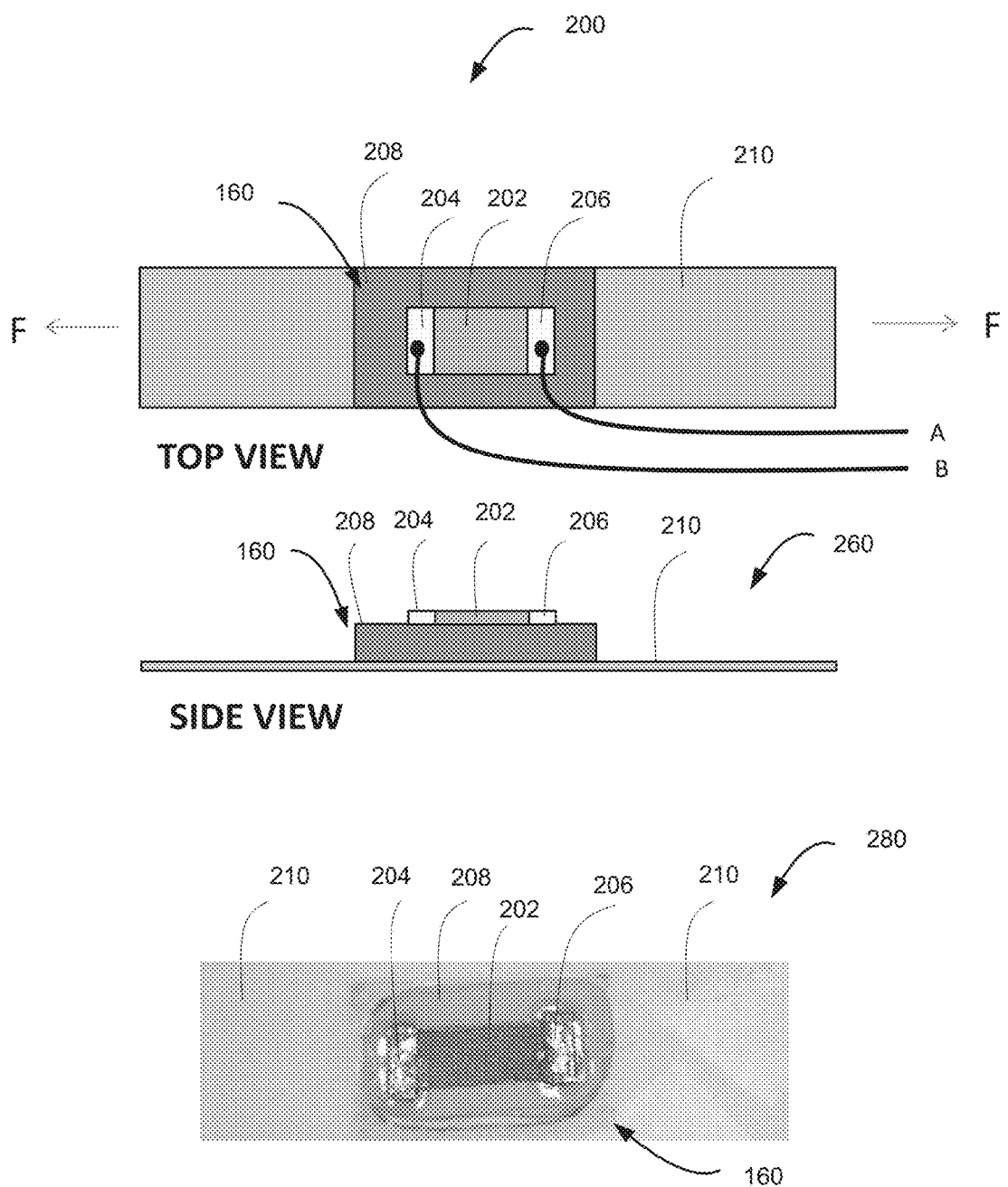
FIG. 2 is a schematic diagram illustrating an example stretch sensor that may be used in a wearable sensor apparatus, in accordance with some embodiments.

FIG. 2 is a schematic diagram illustrating an example stretch sensor that may be used in a wearable sensor apparatus, in accordance with some embodiments. More specifically, FIG. 2 illustrates a top view 200, side view 260, and implementation 280 of the stretch sensor, such as sensor 160 described in reference to FIG. 1. The described embodiments may utilize conductive fabric as a stretch sensing device, as explained below.

As known, conductive fabrics may be used in flexible shielding systems to shield electronic components from electromagnetic interference, in e-textiles, and the like. Some conductive fabrics (e.g. Medtex 180, which are made from silver coated nylon) may also be used in medical applications for wound dressing due to their anti-microbial properties. Certain conductive fabrics (such as Medtex 180) may demonstrate a repeatable change in their electrical characteristics (e.g., resistance) in response to stretching that may be caused by application of an external force.

The conductive fabrics may demonstrate the change in resistance in a relatively limited dynamic range before they saturate. For example, conductive fabrics may be stretched about 10% of their original length to get a corresponding (e.g., proportional) change (e.g., increase) in resistance before they saturate. In other words, conductive fabric resistance may remain constant if the fabric is stretched more than about 10% of its original length. The conductive fabrics may also exhibit deformation (creep) when stretched beyond a certain limit, for example, beyond about 20% of their original length.

The described embodiments provide for dissipation of external forces applied to conductive fabric, so as to prevent the conductive fabric from getting stretched beyond a certain length that may correspond to saturation, e.g., beyond 10% of its original length. The magnitude of dissipation may define a limit of the external force that may be applied to the conductive fabric. Accordingly, the external force may be measured using conductive fabric stretching capabilities, within a determined range of stretch of the conductive fabric.

For example, conductive fabric may be used as a resistive stretch transducer if mounted on a flexible substrate, such as elastomeric substrate with determined elasticity, for example, silicone or latex rubber of suitable thickness. This approach may provide for desired range of stretch force measurement via force dissipation and may reduce creep by utilizing elastic properties of the flexible substrate.

Referring to FIG. 2, the sensor 160 may include a conductive fabric component 202 of a determined length. As described above, the conductive fabric component 202 may act as a resistive stretch sensor as its resistance changes (e.g., increases) in response to a stretch of the conductive fabric component 202. For example, resistance of conductive fabric component 202 in non-stretched condition may be about 10 ohms and may increase to about 12 ohms in response to stretching.

The conductive fabric component 202 may include electrical contacts 204, 206 that may be disposed around respective ends of the conductive fabric component 202 as shown, to provide readings of an electrical parameter (e.g., resistance) generated by the stretch sensor 160 in response to a stretch of the conductive fabric component 202. In embodiments, the electrical contacts 204, 206 may comprise adhesive copper foil, conductive paint, conductive glue, or the like. Conductive wires A and B may be used to provide electrical connections to electrical contacts 204, 206, e.g., by soldering or by means of conductive glue. The resistance change between wires A and B may be converted to a (e.g., proportional) voltage output by the circuitry 144, which is described in detail in reference to FIG. 3.

The conductive fabric component 202 may be disposed, e.g., attachably mounted on a flexible substrate 208 having a determined (first) thickness. The flexible substrate 208 may be attachably mounted on another flexible substrate 210 of a determined (second) thickness. The first thickness of the flexible substrate 208 may be greater than the second thickness of the flexible substrate 210. The substrates 208 and 210 may comprise an elastomer (e.g., silicone elastomer), a polymer, and the like. An external force F may be applied to the flexible substrate 208 (and correspondingly, to the conductive fabric component 202) directly or indirectly (e.g., via the substrate 210, as shown). The conductive fabric component 202, in response to a direct or indirect application of external force F to the flexible substrate 208, may stretch between the determined (first) length and a second length that is greater than the first length, and to generate an electric parameter (e.g., resistance) based on the external force F applied in direction as shown. In embodiments, the electric parameter (e.g., resistance) generated may be proportional to the external force F applied.

A desired portion of the external stretch force F may be dissipated in causing a stretch of the thinner substrate 210. The thicker substrate 208 may be stretched by a fraction compared to the total elongation (stretch) of thinner substrate 210. The conductive fabric component 202 is mounted on the thicker substrate 208 and may be subjected to a desired stretch (e.g., about 10% of its length) by relatively large external force F applied to the substrate 210. Accordingly, the conductive fabric component 202 may be prevented from getting saturated by substantial stretch force F.

The range of measurement of external force F by the stretch sensor 160 may be controlled by the relative thicknesses of substrates 208 and 210, e.g., the ratio of thicknesses of substrates 208 and 210. The sensitivity of the stretch sensor 160 and its dynamic range may be adjusted to a desired level by choosing the desired relative thicknesses (e.g., ratio) of substrates 208 and 210. The larger the relative thickness, the larger the dynamic range of measurements and smaller the sensitivity to stretching of the stretch sensor 160.

As described, the conductive fabric component 202 may be mounted on the flexible substrate 208, which may be mounted on the flexible substrate 210. Both substrates 208, 210 may comprise elastomers with desired elasticity. Accordingly, the substrates 208, 210 may substantially instantly regain their original shape and length after external stretch force F is removed. In turn, the conductive fabric component 202 may also be compelled to regain its original length, thereby reducing or eliminating creep. The thickness of the flexible substrate 208 may ensure that the conductive fabric component 202 remains within a desired range of stretch (e.g., may not be stretched more than 10% of its original length) in response to external force F that may be applied in a practical application of a wearable sensor apparatus utilizing the stretch sensor, such as apparatus 100.

A wearable sensor apparatus implemented with the stretch sensor as described above may provide a number of advantages compared to conventional wearable sensor device solutions. For example, the described stretch sensor 160 may be realized in a desired (e.g, relatively small) form factor, such as about 10 mm×20 mm×3 mm, and in a desired profile and weight, depending on thicknesses of flexible substrates 208, 210. Accordingly, the stretch sensor 160 may be integrated into small wearable devices such as the strap of a wrist watch. The described stretch sensor 160 may be conformal with the user's body shape and suitable for various wearable device applications, such as wearables or smart clothing. In some instances, multiple wearable sensor apparatuses configured with the stretch sensor described above may apply to a user's body to form a body area network, enabling a host of different applications.

Further, the stretch sensor 160 characteristics may be highly repeatable and stable over a desired period of time because the sensor 160 may be configured to regain its original size, shape, and resistance substantially instantly and substantially without creep. Also, the dynamic range and sensitivity of the stretch sensor may be adjusted by choosing the thicknesses of flexible substrates 208, 210. Also, the stretch sensor 160 described above may require lower power supply than known conventional stretch sensors.

Figure 3:
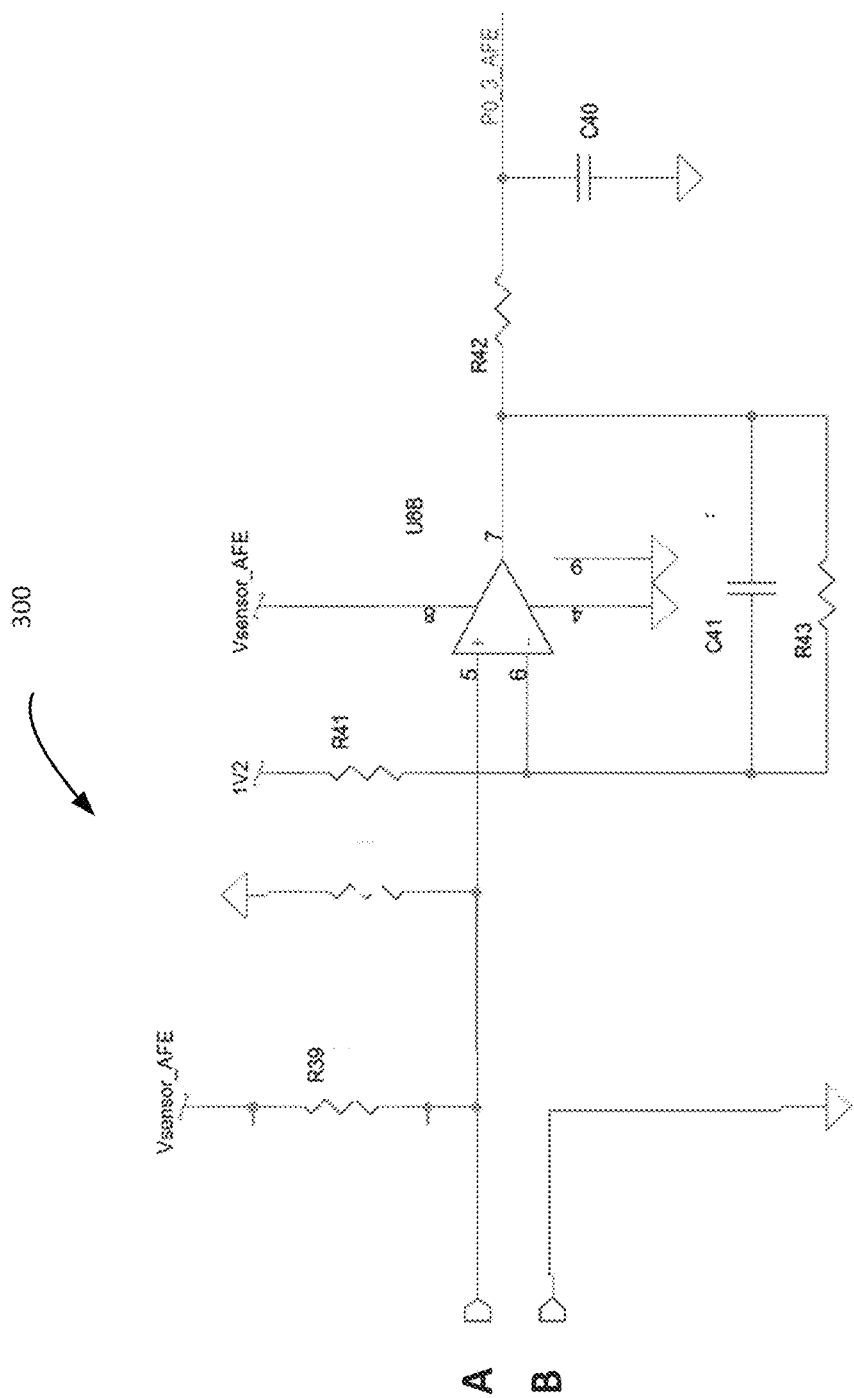
FIG. 3 is a schematic diagram of an example implementation of a circuitry configured to process the readings provided by a stretch sensor of a wearable sensor apparatus, in accordance with some embodiments.

FIG. 3 is a schematic diagram of an example implementation of a circuitry configured to process the readings provided by a stretch sensor of a wearable sensor apparatus, in accordance with some embodiments. More specifically, the schematic diagram of FIG. 3 may provide circuitry 300 comprising an example at least partial implementation of the circuitry 144 of the apparatus 100 of FIG. 1. In embodiments, the stretch sensor 160 may be coupled with the circuitry 300 at input points A, B, corresponding to electrical wires A and B of FIG. 2.

As described, a change in resistance of the stretch sensor 160 may occur when the conductive fabric component 202 is stretched. Input points A and B and resistance R39 may form a resistive potential divider circuit coupled with the electrical contacts 204, 206, to generate voltage in response to a change in resistance caused by the stretch of the conductive fabric component 202. The potential divider circuit may be excited by a direct current (DC) voltage source Vsensor_AFE. Changes in resistance cause voltage changes at point A, which are fed to the input of an amplifier U8B coupled to the resistive potential divider circuit. As resistance of the fabric component of the stretch sensor 160 changes, it causes a corresponding (e.g., proportional) voltage change at the input of the amplifier U8B. The amplifier U8B may be configured to receive the generated voltage and to provide an output voltage signal that is corresponding (e.g., proportional) to the stretch of the conductive fabric component 202. Resistances R43 and R41 may be used to set the gain (amplification) of the voltage, depending on the application of the apparatus 100. 1V2 may be a reference voltage applied to R41. Elements C41, R43 and R42, C40 may form low pass filters to remove high frequency noise and preserve low frequency stretch signal. The cut-off frequency of these filters may be selected depending on the application of the apparatus 100. The output signal P0_3_AFE comprises a signal which corresponds (e.g., proportional) to the stretch of the sensor 160 and may be connected to an input of an ADC (not shown) for digitization and further processing.

Figure 4:
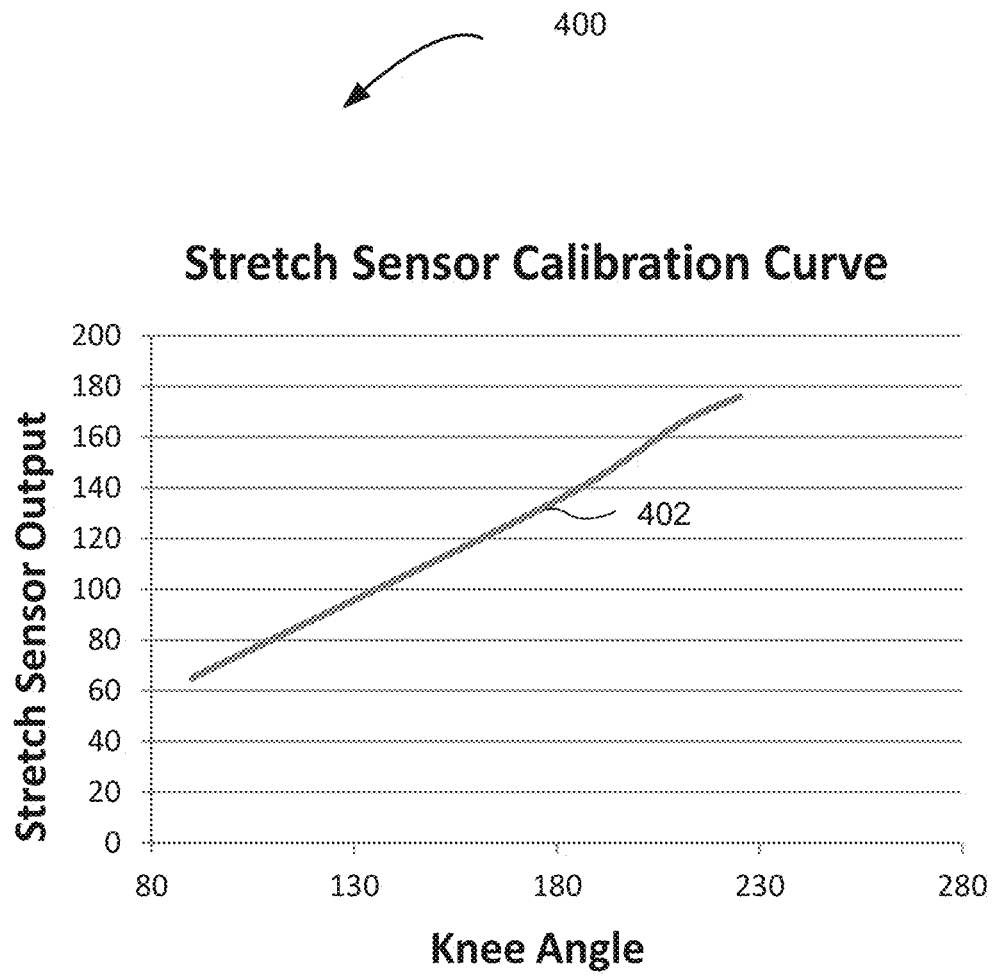
FIG. 4 is a graph illustrating a stretch sensor output as function of an applied external force, in accordance with embodiments.

FIG. 4 is a graph illustrating a stretch sensor output as function of an applied external force, in accordance with embodiments. More specifically, graph 400 illustrates the output of the stretch sensor (e.g., resistance) used in an application to a wearable knee band described below. As shown, the sensor output provides a substantially linear dependency from applied external force, manifested in a knee bend angle. The stretch sensor may be calibrated for measuring an external force within the desired range. In FIG. 4 the desired force measurement range corresponds to the knee angle range. Accordingly, the stretch sensor may be calibrated to measure the knee bend angle within a desired angle range, to provide a substantially linear curve 402. As described above, such calibration may be accomplished by a selection of the relative (e.g. ratio of) thicknesses of flexible substrates 208, 210 (FIG. 2). In alternate embodiments, the sensor output may provide non-linear response to the applied external force.

The wearable sensor apparatus (e.g., apparatus 100 having stretch sensor 160) described in reference to FIGS. 1-3 may be used in a variety of applications. For example, the apparatus 100 may comprise a wearable conformal motion sensing system that may be used, for example, in rehabilitation (e.g., physiotherapy) of the joints, sports applications, and the like. Such conformal motion sensing system may be wrapped around different user body parts such as chest, knee, wrist, neck, etc.

FIGS. 5-8 illustrate different views of an example wearable sensor apparatus 100 comprising a conformal motion sensing system, in accordance with some embodiments. For example, the conformal motion sensing system may be used on any human joint in connection with knee bands, ankle caps, vests, garments (e.g., tight fitting garments), and the like.

FIG. 5 illustrates a conformal motion sensing system 500 mounted (e.g., removably attached) on a knee band 502. The conformal motion sensing system 500 may include the components of the apparatus 100. For example, conformal motion sensing system 500 may include the flexible substrate 102. As shown, the conformal body 102 may comprise a conformal band, which may house the components of apparatus 100. More specifically, the conformal body 102 may house the stretch sensor 160, other sensors (e.g., 104, 106), IMU wiring (shown in FIG. 6), digital node 192, IMU 110, wiring 114, sensor front end module 142, and IMU 108 (not visible in FIG. 5). For measuring joint motion, the conformal motions sensing system 500 may be configured such that the IMU 108 and 110 may be placed on either sides of the joint.

As described in reference to FIG. 1, the digital node 192, which integrates compute components, radio, and battery to power the components of the conformal motion sensing system 500, may be coupled with the system 500 via the interface 150 (e.g., a connector, not shown).

FIG. 6 illustrates the conformal motion sensing system 500 detached from the knee band, in accordance with some embodiments. As shown, IMU wiring 116 electrically connecting IMU 110 with sensor front end node 142 (not shown) may comprise a multi-wire bus 602 having a meandering (e.g., sine wave type, zig-zag shaped) pattern deposited inside the conformal body 102.

Figure 7:
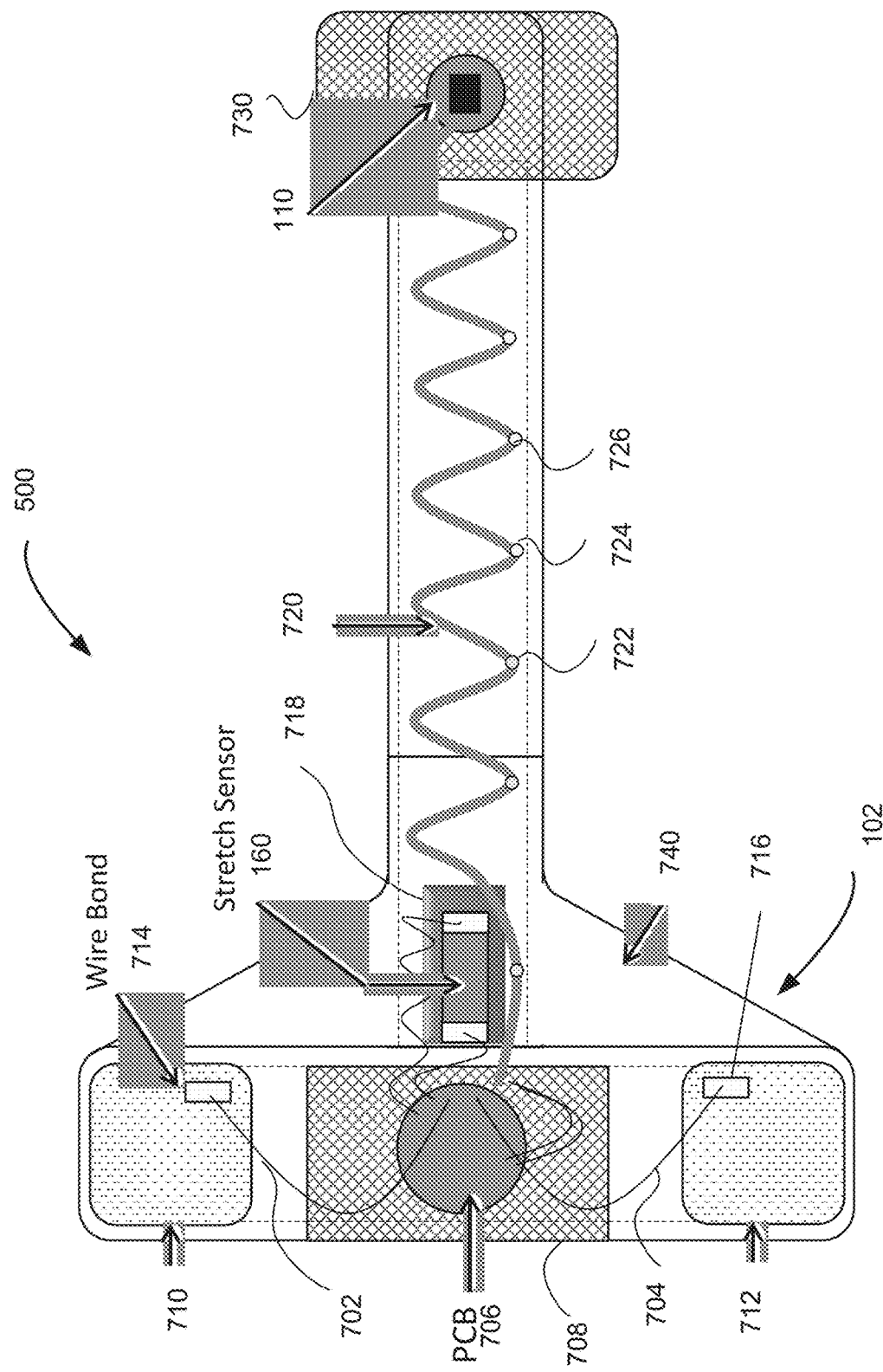
Figure 8:
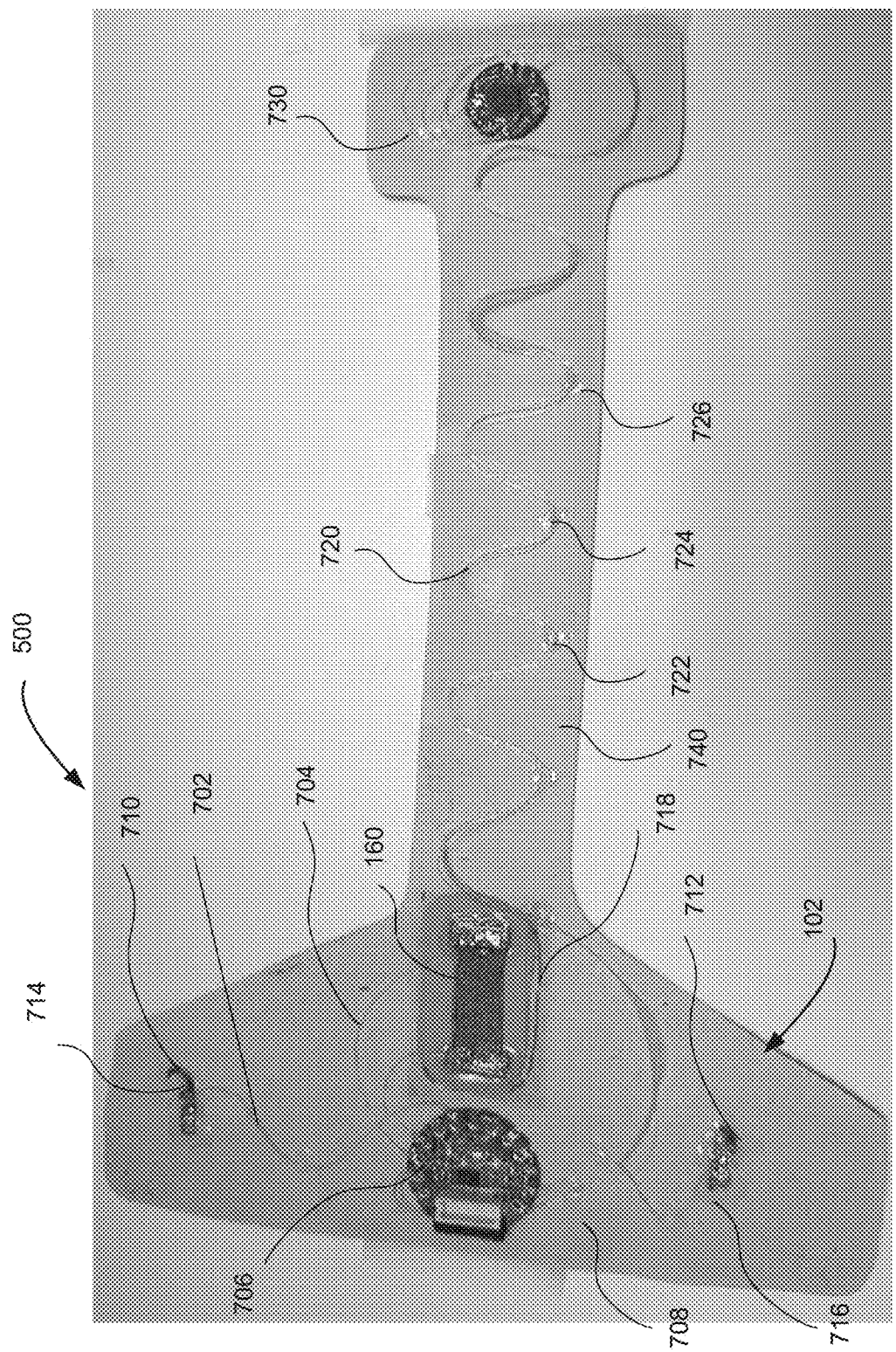

FIGS. 7 and 8 illustrate example diagrams of a conformal motion sensing system including a stretch sensor, in accordance with some embodiments. Specifically, FIG. 7 illustrates an example configuration of the conformal motion sensing system 500, and FIG. 8 illustrates an example implementation of the conformal motion sensing system 500. The description below includes references to the components of FIG. 1 as they may be implemented in the example conformal motion system 500.

Referring to FIGS. 7 and 8, a substrate 740 forming the conformal body 102 may be created on a base elastic substrate (e.g. silicone rubber or latex rubber sheet), then covered and sealed from all sides by another overlaid layer of a thin elastomer sheet, as described below. Electrical connections between different components on the substrate 740, corresponding to wiring 114 of FIG. 1, may comprise ultra-thin, Teflon® insulated, multi-strand wires 702, 704.

A PCB 706 may include the sensor front end module 142 with circuitry 144 and interface connector 150 to the digital node 192 and may be mounted on the substrate 740 on a backing material. The sensors 104, 106 may comprise flexible EMG electrodes 710, 712 that may be glued to the substrate 740 and wire-bonded using, e.g., conductive glue or a solder-able copper tape. The wire bonding areas are indicated by numerals 714, 716. The conductive fabric-based stretch sensor 160 may be glued to the substrate 740 on a backing material 718, wire-bonded and connected to the PCB 706.

The substantially triangular shape of the conformal body 102 and the backing material 718 under the stretch sensor 160 may provide for dissipating excessive stretch forces on the stretch sensor 160, thereby preventing the stretch sensor 160 from getting saturated. In embodiments, the backing material 718 may correspond to the flexible substrate 208, and the substrate 740 may correspond to the flexible substrate 210 of FIG. 2.

IMU 110 may be mounted about an end of the substrate 740 on a backing material 730, as shown. The PCB 706 may supply power to IMU 110. The readings (data signals) from IMU 110 may be routed back to the PCB 706 for processing and further transmission by the digital node 192. As described above, the system 500 may be worn on a user's body, for example on a knee. When the knee is fully flexed, the distance between PCB 706 and IMU 110 may increase to more than 50% of the original distance (e.g., before the body 102 is stretched). To withstand this stretching, a multi-wire bus 720 (corresponding to IMU wiring 116) configured to carry power, ground and signal lines may be used. The bus 720 may use Teflon® coated wires and may be laid on the substrate 740 in a sine wave meandering pattern, as shown. The bus 720 may be anchored (e.g., glued) to the substrate 740 at multiple spots indicated by numerals 722, 724, 726. When internal electrical connections are made, another (e.g., thinner) flexible substrate (e.g., elastomer sheet, not shown) may be overlaid on top of the substrate 740, forming the conformal body 102 and ultimately a fully assembled conformal motion sensing system 500. The overlaid elastomer sheet and the base substrate may be sealed throughout the periphery using a stretchable adhesive, for example.

Figure 9:
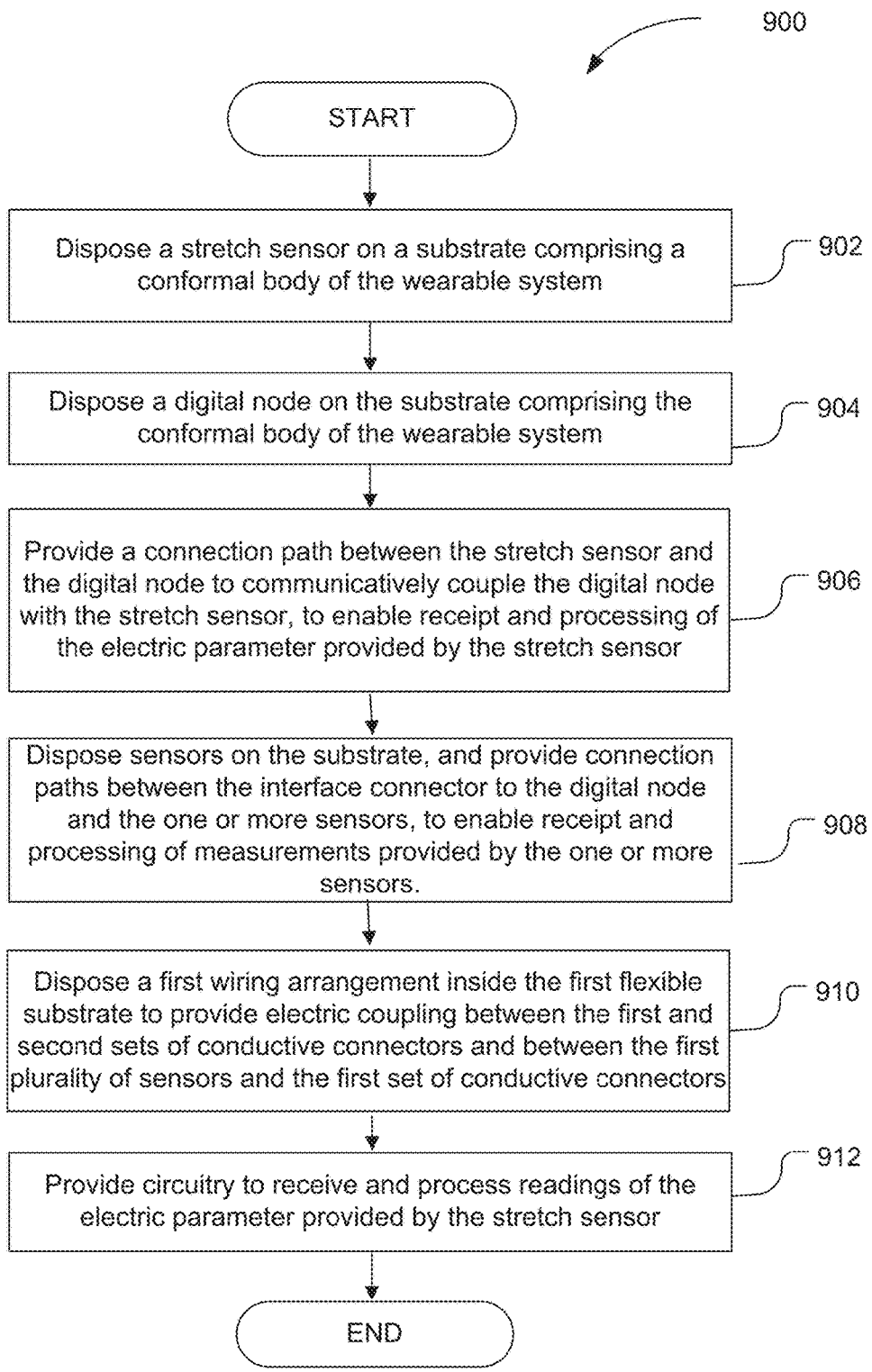
FIG. 9 is a process flow diagram for assembling a wearable sensor apparatus, such as a conformal (e.g., wearable) motion sensing system, in accordance with some embodiments.

FIG. 9 is a process flow diagram for assembling a wearable sensor apparatus, such as a conformal (e.g., wearable) motion sensing system, in accordance with some embodiments. The process 900 may comport with some of the apparatus embodiments described in reference to FIGS. 1-8. In alternate embodiments, the process 900 may be practiced with more or less operations, or different order of the operations.

The process 900 may begin at block 902 and include disposing a stretch sensor (e.g., 160) on a substrate comprising a conformal body 506 of the conformal motion sensing system. The stretch sensor may a flexible substrate and a conductive fabric component that comprises a first length and that is attachably mounted on the flexible substrate, as discussed in reference to FIGS. 2-3. The conductive fabric component, in response to a direct or indirect application of external force to the flexible substrate, may stretch between the first length and a second length that is greater than the first length, and generate an electric parameter based at least in part on an amount of (e.g., in proportion to) the applied external force.

At block 904, the process 900 may include disposing a digital node on the substrate comprising the conformal body of the wearable system. Disposing the digital node on the substrate may include mounting a printed circuit board (PCB) on the substrate, PCB including the interface connector 150 to the digital node 192, as described in reference to FIGS. 1 and 7-8.

At block 906, the process 900 may include providing a connection path between the stretch sensor and the digital node to communicatively couple the digital node with the stretch sensor, to enable receipt and processing of the electric parameter provided by the stretch sensor. The connection path may comprise wiring 114 described in reference to FIGS. 1 and 7-8.

At block 908, the process 900 may include disposing one or more sensors on the substrate, which may include providing connection paths between the interface connector to the digital node and the one or more sensors, to enable receipt and processing of measurements provided by the one or more sensors. The sensors may include sensors 104 and 106, and connection paths may comprise wiring 114 of FIG. 1.

At block 910, the process 900 may include disposing one or more inertial measurement units (IMU) around the conformal body, and providing wired connection paths between the IMU and the PCB, to enable receipt and processing of measurements provided by the IMU. The IMU may comprise IMU 110 and 108 of FIG. 1. Connection paths may comprise, in part, IMU wiring 116 and wiring 114 of FIG. 1.

At block 912, the process 900 may include providing circuitry (e.g., 142 of FIG. 1) to receive and process readings of the electric parameter provided by the stretch sensor, including disposing the circuitry in the PCB or in the digital node and communicatively coupling the circuitry with the digital node.

Figure 10:
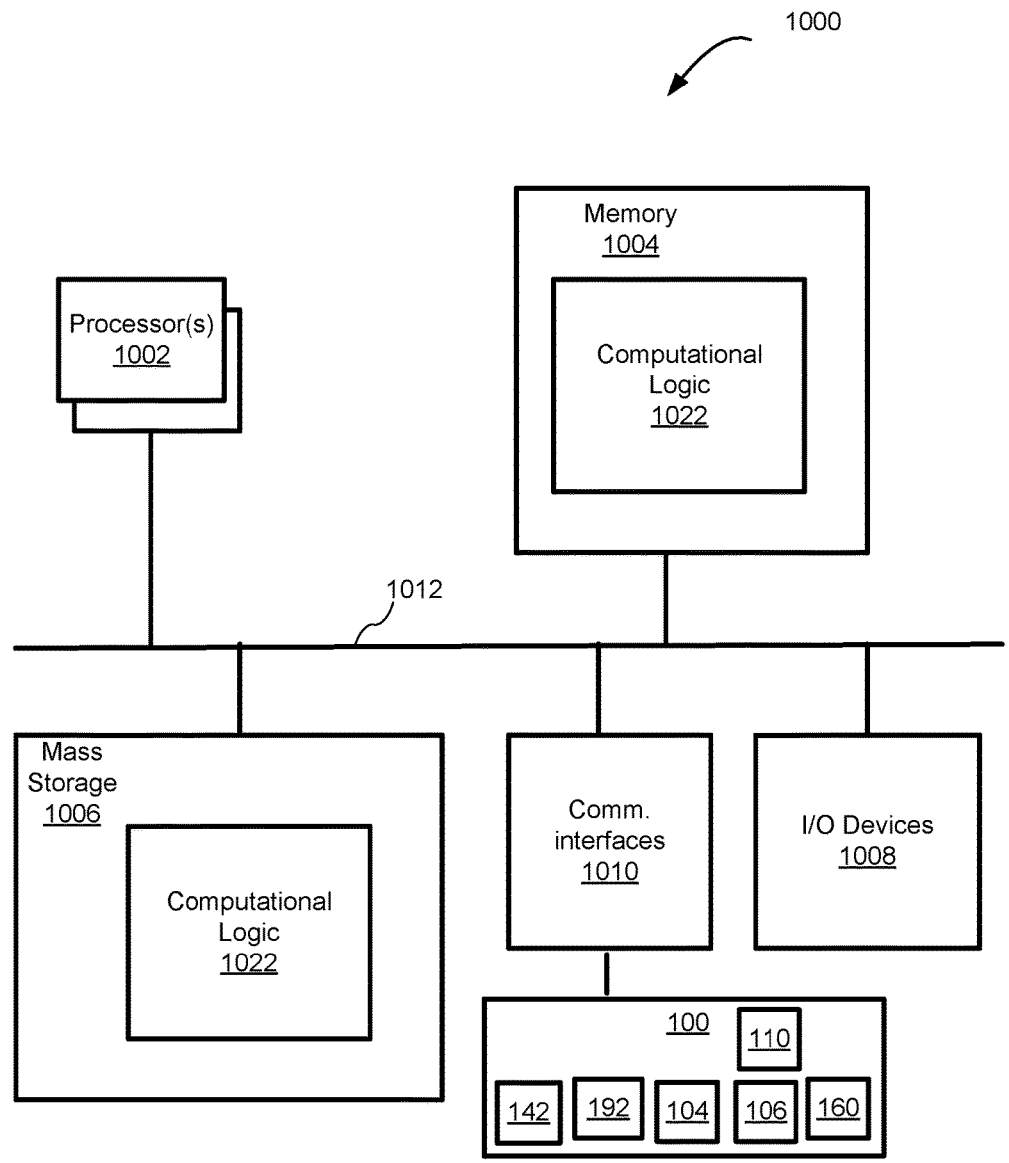
FIG. 10 illustrates an example computing device 1000 suitable for use with various components of FIG. 1 and/or FIG. 5-8, such as wearable sensor apparatus comprising a conformal motion sensing system, in accordance with various embodiments.

FIG. 10 illustrates an example computing device 1000 suitable for use with various components of FIG. 1, such as wearable sensor apparatus 100 of FIG. 1 and/or conformal motion sensing system 500 of FIGS. 5-8, in accordance with various embodiments. In some embodiments, various components of the example computing device 1000 may be used to configure the digital node 192. In some embodiments, various components of the example computing device 1000 may be used to configure the external device 184. As shown, computing device 1000 may include one or more processors or processor cores 1002 and system memory 1004. For the purpose of this application, including the claims, the terms "processor" and "processor cores" may be considered synonymous, unless the context clearly requires otherwise. The processor 1002 may include any type of processors, such as a central processing unit (CPU), a microprocessor, and the like. The processor 1002 may be implemented as an integrated circuit having multi-cores, e.g., a multi-core microprocessor. The computing device 1000 may include mass storage devices 1006 (such as solid state drives, volatile memory (e.g., dynamic random-access memory (DRAM), and so forth). In general, system memory 1004 and/or mass storage devices 1006 may be temporal and/or persistent storage of any type, including, but not limited to, volatile and non-volatile memory, optical, magnetic, and/or solid state mass storage, and so forth. Volatile memory may include, but is not limited to, static and/or dynamic random-access memory. Non-volatile memory may include, but is not limited to, electrically erasable programmable read-only memory, phase change memory, resistive memory, and so forth. System memory 1004 and/or mass storage devices 1006 may include respective copies of programming instructions configured to perform operations related to digital node 192, for example, collectively denoted as computational logic 1022.

The computing device 1000 may further include input/output (I/O) devices 1008 (such as a display, soft keyboard, touch sensitive screen, image capture device, and so forth) and communication interfaces 1010 (such as network interface cards, modems, infrared receivers, radio receivers (e.g., Near Field Communication (NFC), Bluetooth, WiFi, 4G/5G LTE), and so forth).

The communication interfaces 1010 may include communication chips (not shown) that may be configured to operate the device 1000 in accordance with a Global System for Mobile Communication (GSM), General Packet Radio Service (GPRS), Universal Mobile Telecommunications System (UMTS), High Speed Packet Access (HSPA), Evolved HSPA (E-HSPA), or Long-Term Evolution (LTE) network. The communication chips may also be configured to operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chips may be configured to operate in accordance with Code Division Multiple Access (CDMA), Time Division Multiple Access (TDMA), Digital Enhanced Cordless Telecommunications (DECT), Evolution-Data Optimized (EV-DO), derivatives thereof, as well as any other wireless protocols that are designated as 3G, 4G, 5G, and beyond. The communication interfaces 1010 may operate in accordance with other wireless protocols in other embodiments.

In embodiments, the computing device 1000 may associate, e.g., via communication interfaces 1010, with a wearable sensor apparatus 100 or system 500. In some embodiments, the apparatus 100 or system 500 may include stretch sensor 160, sensors 104, 106, IMU 110, coupled with sensor front end module 142 and digital node 192, and may be communicatively coupled with the external device 184 implemented as computing device 1000 described herein.

The above-described computing device 1000 elements may be coupled to each other via system bus 1012, which may represent one or more buses. In the case of multiple buses, they may be bridged by one or more bus bridges (not shown). Each of these elements may perform its conventional functions known in the art. In particular, system memory 1004 and mass storage devices 1006 may be employed to store a working copy and a permanent copy of the programming instructions implementing the operations associated with the wearable sensor apparatus 100, such as the digital node 192 of FIG. 1. The various elements may be implemented by assembler instructions supported by processor(s) 1002 or high-level languages that may be compiled into such instructions.

The permanent copy of the programming instructions of computational logic 1022 may be placed into permanent storage devices 1006 in the factory, or in the field, through, for example, a distribution medium (not shown), such as a compact disc (CD), or through communication interface 1010 (from a distribution server (not shown)). That is, one or more distribution media having an implementation of the agent program may be employed to distribute the agent and to program various computing devices.

The number, capability, and/or capacity of the elements 1008, 1010, 1012 may vary, depending on whether computing device 1000 is used as a stationary computing device, such as a set-top box or desktop computer, or a mobile computing device, such as a tablet computing device, laptop computer, game console, or smartphone. Their constitutions are otherwise known, and accordingly will not be further described.

At least one of processors 1002 may be packaged together with memory having computational logic 1022 configured to practice aspects of embodiments described in reference to FIGS. 1-8. For one embodiment, at least one of processors 1002 may be packaged together with memory having computational logic 1022 to form a System in Package (SiP) or a System on Chip (SoC). For at least one embodiment, the SoC may be utilized in, e.g., but not limited to, a computing device, such as external device 184 of FIG. 1. In another embodiment, the SoC may be utilized to form the digital node 192 of FIG. 1.

In various implementations, the computing device 1000 may comprise a laptop, a netbook, a notebook, an ultrabook, a smartphone, a tablet, a personal digital assistant (PDA), an ultra mobile PC, a mobile phone, or a digital camera. In further implementations, the computing device 1000 may be any other electronic device that processes data.

Example 1 is an apparatus, comprising: a flexible substrate and a conductive fabric component that comprises a first length and that is attachably mounted on the flexible substrate, wherein the conductive fabric component, in response to a direct or indirect application of external force to the flexible substrate, is to stretch between the first length and a second length that is greater than the first length, and to generate an electric parameter based at least in part on an amount of the applied external force.

Example 2 may include the subject matter of Example 1, wherein the flexible substrate is a first flexible substrate, wherein the apparatus further comprises a second flexible substrate, wherein the first flexible substrate is attachably mounted on the second flexible substrate, wherein the external force is applied to the second flexible substrate.

Example 3 may include the subject matter of Example 2, wherein the first flexible substrate comprises a first thickness and the second flexible substrate comprises a second thickness, wherein the first thickness is greater than the second thickness, wherein a range of the application of external force corresponds to the first thickness and the second thickness, wherein the range of the application of external force is to enable the stretch of the conductive fabric component between the first and second lengths.

Example 4 may include the subject matter of Example 2, wherein the first and second flexible substrates include at least a selected one of: elastic fabric, elastomer, or polymer, wherein the application of external force corresponds to a ratio of the first thickness to the second thickness.

Example 5 may include the subject matter of Example 2, wherein the second flexible substrate is stretchable to a third length, wherein the third length is by at least an order of magnitude greater than the second length.

Example 6 may include the subject matter of Example 1, further comprising: electrical contacts disposed around respective ends of the conductive fabric component, to provide readings of the electrical parameter generated in response to the stretch of the conductive fabric component between the first and second lengths; and circuitry coupled with the electrical contacts, to receive and process readings of the electric parameter.

Example 7 may include the subject matter of Example 6, wherein the electric parameter comprises resistance, wherein the circuitry includes: a resistive potential divider circuit coupled with the electrical contacts, to generate voltage in response to a change in resistance caused by the stretch of the conductive fabric component; and an amplifier coupled to the resistive potential divider circuit, to receive the generated voltage and to provide an output voltage signal in response to the stretch of the conductive fabric component.

Example 8 may include the subject matter of any of Examples 1 to 7, wherein the second length is greater than the first length by about 10% of the first length.

Example 9 may include the subject matter of Example 2, wherein the apparatus is a wearable system having a body conformal to a human body part, wherein the second flexible substrate is disposable on the conformable body of the wearable system.

Example 10 may include the subject matter of Example 9, wherein the conformal body includes the second flexible substrate.

Example 11 may include the subject matter of Example 9, wherein the apparatus further comprises: one or more inertial measurement units (IMU) disposed around the conformal body; and a digital node communicatively coupled with the one or more IMU, to supply power to the one or more IMU and to receive, convert, and process the measurements provided by the IMU and to provide the processed measurements to an external aggregating device for further processing.

Example 12 may include the subject matter of Example 11, wherein the digital node is communicatively coupled with the one or more IMU via respective one or more wired connections that are disposed in the conformal body of the wearable system.

Example 13 may include the subject matter of Example 11, further comprising one or more sensors disposed in the conformal body and communicatively coupled with the digital front end node, to provide readings of the sensors to the digital node.

Example 14 may include the subject matter of Example 13, wherein the one or more sensors include at least selected ones of: electromyography (EMG) sensors, temperature sensors, sweat chemical sensors, or motion sensors.

Example 15 may include the subject matter of Example 14, wherein the wearable system comprises a wearable knee strap, a wearable chest strap, a wearable neck strap, a wearable wrist strap, or a wearable foot strap, wherein the external aggregating device comprises a mobile computing device.

Example 16 is a wearable system, comprising: a stretch sensor, including a flexible substrate and a conductive fabric component that comprises a first length and that is attachably mounted on the flexible substrate, wherein the conductive fabric component, in response to a direct or indirect application of external force to the flexible substrate, is to stretch between the first length and a second length that is greater than the first length, and to generate an electric parameter based at least in part on an amount of the applied external force; and circuitry communicatively coupled with the stretch sensor, wherein the circuitry is to receive and process readings of the electric parameter provided by the stretch sensor.

Example 17 may include the subject matter of Example 16, wherein the wearable system further comprises: a body that is conformal to a human body part; one or more inertial measurement units (IMU) disposed around the conformal body; and a digital node communicatively coupled with circuitry and the one or more IMU, to: supply power to the one or more IMU; receive, convert, and process the measurements provided by the IMU and the electric parameter provided by the stretch sensor; and provide the processed measurements to an external aggregating device for further processing.

Example 18 may include the subject matter of Example 17, wherein the flexible substrate is a first flexible substrate, wherein the wearable system further comprises a second flexible substrate, wherein the first flexible substrate is attachably mounted on the second flexible substrate, wherein the second flexible substrate is disposable on the conformable body of the wearable system.

Example 19 may include the subject matter of Example 17, wherein the digital node is communicatively coupled with the one or more IMU via respective one or more wired connections that are disposed in the conformal body of the wearable system.

Example 20 may include the subject matter of Example 17, wherein the one or more wired connections comprise a multi-wire bus to carry a power signal, ground, and one or more signals corresponding to the one or more IMU.

Example 21 may include the subject matter of Example 17, further comprising one or more sensors disposed in the conformal body and communicatively coupled with the digital front end node, to provide readings of the sensors to the digital node.

Example 22 is a method of fabricating a wearable system, comprising: disposing a digital node on a substrate comprising a conformal body of the wearable system; disposing a stretch sensor on the substrate, the stretch sensor including a flexible substrate and a conductive fabric component that comprises a first length and that is attachably mounted on the flexible substrate, wherein the conductive fabric component, in response to a direct or indirect application of external force to the flexible substrate, is to stretch between the first length and a second length that is greater than the first length, and to generate an electric parameter based at least in part on an amount of the applied external force; and providing a connection path between the stretch sensor and the digital node to communicatively couple the digital node with the stretch sensor, to enable receipt and processing of the electric parameter provided by the stretch sensor.

Example 23 may include the subject matter of Example 22, wherein disposing the digital node on the substrate includes mounting a printed circuit board (PCB) on the substrate, the PCB including at least an interface connector to the digital node, wherein the method further comprises: disposing one or more sensors on the substrate; and providing connection paths between the interface connector to the digital node and the one or more sensors, to enable receipt and processing of measurements provided by the one or more sensors.

Example 24 may include the subject matter of Example 23, further comprising: disposing one or more inertial measurement units (IMU) around the conformal body; and providing wired connection paths between the IMU and the PCB, to enable receipt and processing of measurements provided by the IMU.

Example 25 may include the subject matter of Example 23, wherein disposing the digital node on the substrate includes providing circuitry to receive and process readings of the electric parameter provided by the stretch sensor, wherein providing includes: disposing the circuitry in the PCB or in the digital node; and communicatively coupling the circuitry with the digital node, wherein disposing a stretch sensor on the substrate comprising a conformal body includes: disposing the stretch sensor on the flexible substrate; and attachably mounting the flexible substrate on the substrate comprising a conformal body.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. An apparatus, comprising:
   a first flexible substrate having a first thickness;
   a second flexible substrate having a second thickness, wherein the second flexible substrate comprises a substantially triangular shape, wherein the first flexible substrate is attachably mounted on the second flexible substrate, wherein the first thickness is greater than the second thickness;
   a conductive fabric component that comprises a first length and that is attachably mounted on the first flexible substrate to form a stretch sensor, wherein the conductive fabric component, in response to an application of an external force to the second flexible substrate, is to stretch between the first length and a second length that is greater than the first length, and to generate an electric parameter based at least in part on an amount of the applied external force, wherein the first thickness of the first flexible substrate and the second thickness of the second flexible substrate define a range of measurements of the applied external force indicated by the electric parameter, wherein the first and second thicknesses are selected to provide a ratio of relative thickness to control the range of measurements of the applied external force and prevent the conductive fabric component from stretching beyond the second length, wherein the triangular shape of the second flexible substrate contributes to the control of the range of measurements of the applied external force.

2. The apparatus of claim 1, wherein an increase of the ratio of the first thickness to the second thickness corresponds to an increase of the range of measurements of the applied external force.

3. The apparatus of claim 1, wherein the first and second flexible substrates include at least a selected one of: elastic fabric, elastomer, or polymer, wherein the application of external force corresponds to the ratio of the first thickness to the second thickness.

4. The apparatus of claim 1, wherein the second flexible substrate is stretchable to a third length, wherein the third length is by at least an order of magnitude greater than the second length.

5. The apparatus of claim 1, further comprising:
electrical contacts disposed around respective ends of the conductive fabric component, to provide readings of the electrical parameter generated in response to the stretch of the conductive fabric component between the first and second lengths; and
circuitry coupled with the electrical contacts, to receive and process readings of the electric parameter.

6. The apparatus of claim 5, wherein the electric parameter comprises resistance, wherein the circuitry includes:
a resistive potential divider circuit coupled with the electrical contacts, to generate voltage in response to a change in resistance caused by the stretch of the conductive fabric component; and
an amplifier coupled to the resistive potential divider circuit, to receive the generated voltage and to provide an output voltage signal in response to the stretch of the conductive fabric component.

7. The apparatus of claim 1, wherein the second length is greater than the first length by about 10% of the first length.

8. The apparatus of claim 1, wherein the apparatus is a wearable system having a body conformal to a human body part, wherein the second flexible substrate is disposable on the conformal body of the wearable system.

9. The apparatus of claim 8, wherein the conformal body includes the second flexible substrate.

10. The apparatus of claim 8, further comprising:
one or more inertial measurement units (IMU) disposed around the conformal body; and
a digital node communicatively coupled with the one or more IMU, to supply power to the one or more IMU and to receive, convert, and process the measurements provided by the IMU and to provide the processed measurements to an external aggregating device for further processing.

11. The apparatus of claim 10, wherein the digital node is communicatively coupled with the one or more IMU via respective one or more wired connections that are disposed in the conformal body of the wearable system.

12. The apparatus of claim 10, further comprising one or more sensors disposed in the conformal body and communicatively coupled with a digital front end node, to provide readings of the sensors to the digital node.

13. The apparatus of claim 12, wherein the one or more sensors include at least selected ones of: electromyography (EMG) sensors, temperature sensors, sweat chemical sensors, or motion sensors.

14. The apparatus of claim 10, wherein the wearable system comprises a wearable knee strap, a wearable chest strap, a wearable neck strap, a wearable wrist strap, or a wearable foot strap, wherein the external aggregating device comprises a mobile computing device.

15. A wearable system, comprising:
a stretch sensor, including:
a first flexible substrate having a first thickness; and
a conductive fabric component that comprises a first length and that is attachably mounted on the first flexible substrate;
a second flexible substrate having a second thickness, wherein the second flexible substrate comprises a substantially triangular shape, wherein the first flexible substrate is attachably mounted on the second flexible substrate, wherein the first thickness is greater than the second thickness;
wherein the conductive fabric component, in response to an application of an external force to the second flexible substrate, is to stretch between the first length and a second length that is greater than the first length, and to generate an electric parameter based at least in part on an amount of the applied external force, wherein the first thickness of the first flexible substrate and the second thickness of the second flexible substrate define a range of measurements of the applied external force indicated by the electric parameter, wherein the first and second thicknesses are selected to provide a ratio of relative thickness to control the range of measurements of the applied external force and prevent the conductive fabric component from stretching beyond the second length, wherein the triangular shape of the second flexible substrate contributes to the control of the range of measurements of the applied external force; and
circuitry communicatively coupled with the stretch sensor, wherein the circuitry is to receive and process readings of the electric parameter provided by the stretch sensor.

16. The wearable system of claim 15, wherein the wearable system further comprises:
a body that is conformal to a human body part;
one or more inertial measurement units (IMU) disposed around the conformal body; and
a digital node communicatively coupled with circuitry and the one or more IMU, to:
supply power to the one or more IMU;
receive, convert, and process the measurements provided by the IMU and the electric parameter provided by the stretch sensor; and
provide the processed measurements to an external aggregating device for further processing.

17. The wearable system of claim 16, wherein the second flexible substrate is disposable on the conformal body of the wearable system, or the conformal body comprises the second flexible substrate.

18. The wearable system of claim 16, wherein the digital node is communicatively coupled with the one or more IMU via respective one or more wired connections that are disposed in the conformal body of the wearable system.

19. The wearable system of claim 16, wherein one or more wired connections comprise a multi-wire bus to carry a power signal, ground, and one or more signals corresponding to the one or more IMU.

20. The wearable system of claim 16, further comprising one or more sensors disposed in the conformal body and communicatively coupled with a digital front end node, to provide readings of the sensors to the digital node.

21. A method of fabricating a wearable system, comprising:
providing a first flexible substrate having a first thickness;
attachably mounting a conductive fabric component that comprises a first length on the first flexible substrate to form a stretch sensor;
attachably mounting the stretch sensor on a second flexible substrate having a second thickness and a substantially triangular shape, wherein the first thickness is greater than the second thickness, wherein the second flexible substrate comprises a body conformal to a human body part,
wherein the conductive fabric component, in response to an application of an external force to the second flexible substrate, is to stretch between the first length and a second length that is greater than the first length, and to generate an electric parameter based at least in part on an amount of the applied external force, wherein providing the first and second flexible substrates includes selecting the first and second thicknesses of the first and second flexible substrates, to provide a ratio of relative thickness to control a range of measurements of the applied external force, and prevent the conductive fabric component from stretching beyond the second length, wherein the triangular shape of the second flexible substrate contributes to the control of the range of measurements of the applied external force;
disposing a digital node on the conformal body; and
providing a connection path between the stretch sensor and the digital node to communicatively couple the digital node with the stretch sensor, to enable receipt and processing of the electric parameter provided by the stretch sensor.

22. The method of claim 21, wherein disposing the digital node on the conformal body includes mounting a printed circuit board (PCB) on the conformal body, the PCB including at least an interface connector to the digital node, wherein the method further comprises:
disposing one or more sensors on the conformal body; and
providing connection paths between the interface connector to the digital node and the one or more sensors, to enable receipt and processing of measurements provided by the one or more sensors.

23. The method of claim 22, further comprising:
disposing one or more inertial measurement units (IMU) around the conformal body; and
providing wired connection paths between the IMU and the PCB, to enable receipt and processing of measurements provided by the IMU.

24. The method of claim 22, wherein disposing the digital node on the conformal body includes providing circuitry to receive and process readings of the electric parameter provided by the stretch sensor, wherein providing includes:
disposing the circuitry in the PCB or in the digital node; and
communicatively coupling the circuitry with the digital node.

\* \* \* \* \*